United States Patent [19]

Key

[11] 3,952,730

[45] Apr. 27, 1976

[54] INSTRUMENT FOR USE IN THE MEASUREMENT OF BLOOD GASES

[75] Inventor: Alan Key, Newbury, England

[73] Assignee: National Research Development Corporation, London, England

[22] Filed: Oct. 22, 1974

[21] Appl. No.: 517,058

[30] Foreign Application Priority Data

Oct. 30, 1973 United Kingdom............... 50392/73

[52] U.S. Cl. .............................. 128/2 G; 128/2 L; 128/214 R; 128/348
[51] Int. Cl.² .......................................... A61B 5/00
[58] Field of Search ......... 128/2 L, 2 E, 2 G, 214.4, 128/348; 117/161 KP

[56] References Cited

UNITED STATES PATENTS

| | | | |
|---|---|---|---|
| 3,336,918 | 8/1967 | Jeckel .......................... | 128/348 UX |
| 3,512,517 | 5/1970 | Kadish et al. ........................ | 128/2 E |
| 3,572,315 | 3/1971 | Cullen ................................. | 128/2 E |
| 3,658,053 | 4/1972 | Fergusson et al. ............... | 128/2 E X |
| 3,726,825 | 4/1973 | Woodward et al. ...... | 117/161 KP X |

OTHER PUBLICATIONS

Wald, A. et al., *Med. & Biol. Engng.* Vol. 8, 1970, pp. 111–128.

*Primary Examiner*—Kyle L. Howell
*Attorney, Agent, or Firm*—Cushman, Darby & Cushman

[57] ABSTRACT

A catheter instrument for use in the continuous measurement of blood gases in vivo by mass spectrometry comprises a flexible mylon tube internally coated with a material such as polyurethane which inhibits outgassing of water vapour from the nylon. A porous body is secured in one end of the tube and has a smoothly rounded projecting portion covered by a gas-permeable membrane. The membrane forms an integral part of a sheath having a further part which fits closely around the nylon tube, the sheath being of a non-thrombogenic polymeric material such as silicone rubber.

3 Claims, 1 Drawing Figure

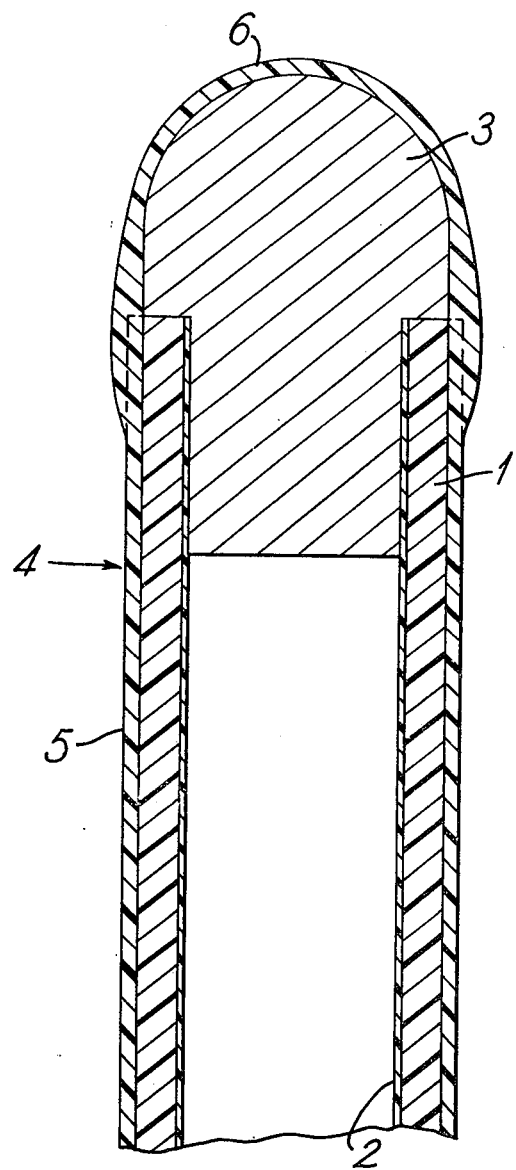

INSTRUMENT FOR USE IN THE MEASUREMENT OF BLOOD GASES

In one known method for the continuous measurement of blood gases in vivo, use is made of an instrument in the form of a flexible catheter which is substantially impermeable to gases and whose distal end is closed by a gas-permeable membrane; the instrument is inserted into the relevant blood vessel and its interior is connected under vacuum to the inlet port of a mass spectrometer. Gases dissolved in the blood diffuse through the membrane and pass along the catheter to the mass spectrometer, in which they are analysed. Such a method is described for example in a paper by Wald et al. in Medical and Biological Engineering, Volume 8, pages 111 – 128, which also discloses a possible form of construction for the instrument in which the membrane is welded to the catheter and is mechanically supported by a porous substrate mounted at the end of the catheter.

In designing such an instrument an obvious first choice for the material of the catheter would be nylon, since it is substantially impervious to atmospheric gases and is readily available in the form of tubing of appropriate sizes. Unfortunately, however, nylon absorbs water very readily, so that in use outgassing from the nylon would occur to such an extent as to make it difficult to obtain safe working conditions for the mass spectrometer. Moreover it is difficult to make a satisfactory joint between a nylon catheter and a membrane of a suitable material such as silicone rubber.

It is an object of the present invention to provide an arrangement enabling these problems to be overcome.

According to the invention, an instrument for use in the measurement of blood gases comprises a flexible catheter in the form of a nylon tube having its internal surface coated with a material which will effectively inhibit outgassing of water vapour into the interior of the tube under vacuum, a rigid porous body secured in one end of the tube and having a smoothly rounded portion projecting from said end, and a sheath of a non-thrombogenic polymeric material part of which fits closely around the tube and part of which constitutes a gas-permeable membrane covering the projecting portion of the porous body.

Preferably said polymeric material is silicone rubber and the material with which the internal surface of the tube is coated is either polyurethane or silicone rubber.

One embodiment of the invention will now be described by way of example with reference to the accompanying drawing, which is a sectional view of part of an instrument suitable for use in the method referred to above.

The instrument comprises a flexible catheter in the form of a nylon tube 1 having an internal diameter of one mm. and an external diameter of 1.34 mm; the tube 1 may typically have a length of about 50 cms. The internal surface of the tube 1 is coated with a layer 2 of polyurethane about 25 microns thick. In one end of the internally coated tube 1 is secured a plug 3 of porous sintered bronze having a maximum particle retention size of 3 – 6 microns. The plug 3 has a portion projecting from the end of the tube 1, this portion being in the form of a hemisphere superimposed on a cylinder of length 0.35 mm., the hemisphere and cylinder both having a diameter equal to the external diameter of the tube 1. The instrument further comprises a sheath 4 of silicone rubber about 75 microns thick, part of which is in the form of a tube 5 which fits closely around the tube 1 and a part of which constitutes a gas-permeable membrane 6 covering the projecting portion of the plug 3. At the end remote from that shown in the drawing, the catheter is provided with a connector (not shown) for coupling the catheter to a mass spectrometer.

The structure illustrated in the drawing may suitably be fabricated as follows. A length of nylon tubing which is to form the tube 1 has sucked into it a quantity of polyurethane varnish sufficient to fill most of its interior, and is then held vertically so as to allow the varnish to drain out under the influence of gravity. The tubing is then left for about one week to allow the resultant coating on the internal surface of the tubing to dry and harden. After trimming of the ends of the nylon tubing, it is blocked at both ends with removable plugs and is then sheathed in an appropriate length of silicone rubber tubing which is to constitute the tube 5 forming part of the sheath 4. The silicone rubber tubing initially has an internal diameter of one mm. and an external diameter of 1.15 mm., and may for example be of the kind supplied by J. G. Franklin & Sons Limited under the Product Code No. 590000. This tubing is immersed in carbon tetrachloride, the absorption of this solvent by the silicone rubber causing the tubing to swell, and the nylon tubing is then inserted into the silicone rubber tubing, the solvent subsequently being allowed to evaporate from the silicone rubber tubing so that it shrinks on to the nylon tubing. The plugs at the ends of the tubing are then removed.

At the end of the tubing at which the plug 3 is to be mounted, the silicone rubber tubing is retracted by rolling it back over a length of about five mm., and the exposed nylon is etched with a primer such as that supplied by Dow Corning Limited under the designation DC.1200. After allowing half an hour for drying, a cold-curing silicone rubber adhesive is applied to the exposed nylon surface, and the silicone rubber tubing is rolled back into place so that it is stuck firmly to the nylon tubing when the adhesive has cured. The bronze plug 3 is then inserted into the end of the tubing, being secured in position with a silicone rubber adhesive.

The sheath 4 is then completed in the following manner. The projecting portion of the plug 3 and a length of less than five mm. of the adjacent tubing are dipped in a dispersion of silicone rubber with a catalyst in toluene, such as is obtainable from Smith & Nephew Limited, and then withdrawn slowly from the dispersion. The toluene is allowed to evaporate and the whole process is then repeated. This results in the formation of a coating on the projecting portion of the plug 3 and on a short length of the silicone rubber tubing. The resultant structure is heated in an oven at a temperature of 150°C. for 30 minutes to drive off the filler and the catalyst and polymerise the silicone rubber of the coating, the membrane 6 thus formed having a thickness of the same order as that of the tube 5. During this polymerisation, the material of the coating becomes integrally bonded to the material of the silicone rubber tubing.

In an alternative procedure for completing the sheath 4 use may be made of a silicone rubber membrane which is initially formed separately from the basic component produced by the steps described above up to the point at which the plug 3 is secured in position. The formation of this membrane is effected by dipping a stainless steel former to a depth of about one cm. in a silicone rubber dispersion similar to that referred to in the preceding paragraph, the forming having a similar shape too but slightly smaller dimensions than the basic component, withdrawing the former slowly from the dispersion, allowing the toluene to evaporate from the dispersion, and then heating the former at a temperature of 150°C for 30 minutes. The membrane is detached carefully from the former, trimmed to a length of about five mm, swollen by immersion in carbon tetrachloride, and applied carefully to the basic component so as to cover the plug 3 and a short length of the adjacent silicone rubber tubing, the carbon tetrachloride then evaporating so that the membrane shrinks to fit tightly in place. The free end of the membrane is rolled back nearly to the end of the tubing, a small amount of a cold-curing silicone rubber adhesive is applied to the outside of the tubing and the membrane is then unrolled back into place, squeezing out most of the adhesive from between it and the tubing. The remaining thin layer of adhesive between the membrane and the silicone rubber tubing forms an integral bond between them as the adhesive cures, the process being completed in about 12 hours. With this method of providing the membrane, smoothing at the initial junction of the membrane and the tubing may if desired be effected by a further coating with silicone rubber in a similar manner to that described above, but using a less viscous dispersion of silicone rubber.

I claim:

1. An instrument for use in the measurement of blood gases, the instrument comprising:
    a flexible catheter in the form of a nylon tube having its internal surface coated with a material which will effectively inhibit outgassing of water vapour into the interior of the tube under vacuum;
    a rigid porous body extending across the whole of the end of said tube, said porous body having a first portion secured within said tube adjacent said end and having a smoothly rounded second portion projecting from said end; and
    a sheath of a non-thrombogenic polymeric material part of which closely envelops said tube and part of which constitutes a gas-permeable membrane completely covering said second portion of said porous body.

2. An instrument according to claim 1, in which said polymeric material is silicone rubber.

3. An instrument according to claim 1, in which the material with which the internal surface of said tube is coated is polyurethane.

* * * * *